United States Patent
Eipel et al.

(10) Patent No.: US 6,737,024 B1
(45) Date of Patent: May 18, 2004

(54) SOLID SUPPORTS FOR ANALYTICAL MEASURING PROCESSES

(75) Inventors: Heinz Eipel, Bensheim (DE); Harald Keller, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/214,868

(22) PCT Filed: Jul. 7, 1997

(86) PCT No.: PCT/EP97/03571

§ 371 (c)(1),
(2), (4) Date: Jan. 14, 1999

(87) PCT Pub. No.: WO98/03257

PCT Pub. Date: Jan. 29, 1998

(30) Foreign Application Priority Data

Jul. 18, 1996 (DE) .......................... 196 28 928

(51) Int. Cl.[7] .............................. G01N 33/48
(52) U.S. Cl. .................. 422/101; 422/61; 422/102; 435/288.4; 435/305.2
(58) Field of Search .................. 422/56, 58, 61, 422/101; 435/286.2, 288.4, 305.2

(56) References Cited

U.S. PATENT DOCUMENTS

| | | |
|---|---|---|
| 4,728,792 A | 3/1988 | Warner et al. |
| 5,041,266 A | 8/1991 | Fox |
| 5,284,753 A * | 2/1994 | Goodwin ............... 435/30 |
| 5,378,638 A | 1/1995 | Deeg et al. |
| 5,545,531 A * | 8/1996 | Rava et al. ............... 435/6 |
| 5,958,203 A * | 9/1999 | Parce et al. ............ 204/451 |

FOREIGN PATENT DOCUMENTS

| | | |
|---|---|---|
| EP | 402 718 | 12/1990 |
| WO | 94/27719 | 12/1994 |
| WO | 95/35505 | 12/1995 |
| WO | 97/22875 | 6/1997 |

OTHER PUBLICATIONS

ASAIO Jrl. Jul.–Sep. 1994, No. 3, Matsuda et al. 594–597.
Jrl. Of Med. Chem. Vol 37, No. 9, Apr. 29, 1994 Gallop et al., 1233–1251.
Jrl. Of Med. Chem. Vol 37, No. 10, May 13, 1994, Gordon et al., 1385–1401.
Sci, Vol 198, Horan et al., 149–156, Oct. 14, 1977.

* cited by examiner

Primary Examiner—Lyle Alfandary-Alexander
(74) Attorney, Agent, or Firm—Keil & Weinkauf

(57) ABSTRACT

The invention relates to solid supports for analytical measurement methods which are essentially composed of an inert solid support material on which hydrophilic measurement zones, separated from one another by a hydrophobic coating, where at least 10 measurement points are applied to the support per $cm^2$. The invention furthermore relates to a process for producing the supports, and to the use of the supports in diagnostic methods, in research looking for active substances, in combinatorial chemistry, in crop protection, in toxicology or in environmental protection.

9 Claims, 2 Drawing Sheets

SOLID SUPPORTS FOR ANALYTICAL MEASURING PROCESSES

Figure 1:
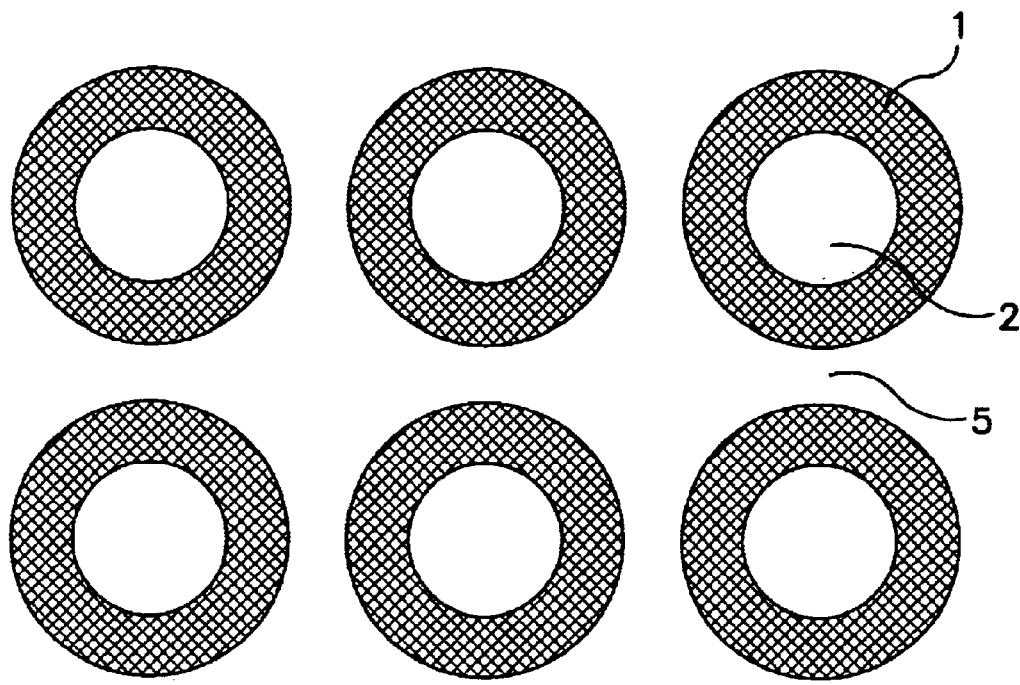

The invention relates to solid supports for analytical measurement methods which are essentially composed of an inert solid support material on which hydrophilic measurement zones which may be provided with a surface loading are separated from one another by at least one hydrophobic coating, where the number of measurement points applied per $cm^2$ of the support is greater than or equal to 10. The invention furthermore relates to a process for producing the supports, and to the use of the supports in diagnostic methods, in research looking for active substances, in combinatorial chemistry, in crop protection, in toxicology or in environmental protection.

A main task of research looking for active substances in crop protection or in medicine is to identify novel lead structures and to develop active substances derived from these structures.

In classical research looking for active substances, the biological effect of novel compounds has been tested in random screening on the whole organism, for example the plant or the microorganism. Employed for this purpose were complex in vitro and in vivo test methods with which only a few hundred substances could be tested each year.

In this case the biological testing was the limiting factor with respect to the synthetic chemistry.

The provision of molecular test systems by molecular and cell biology has led to a drastic change in the situation. These molecular test systems, such as receptor binding assays, enzyme assays or cell-cell interaction assays, can, as a rule, readily be carried out in microtiter plates in reaction volumes of from 50 to 250 µl and can easily be automated. Automation and miniaturization of these test systems permits the sample throughput to be high. This development makes it possible to test large numbers of different chemicals for possible use as lead structure in research looking for active substances.

A modern automated test system allows 100,000 or more chemicals to be tested for their biological effect each year in mass screening. Microtiter plate assays are very often used because, as a rule, they entail low costs, are very reliable and have little susceptibility to faults.

In order to be able fully to exploit the efficiency of these test systems, novel solid-phase syntheses have been and are still being developed in combinatorial chemistry.

Combinatorial chemistry makes it possible to synthesize a wide variety of different chemical compounds, called substance libraries. This is particularly true when combinatorial chemistry makes use of automated solid-phase synthesis (see, for example, review articles I. [sic] Med. Chem. 37 (1994) 1233 and 1385). Solid-phase synthesis has the advantage that a large number of compounds can be synthesized, and that by-products and excess reactants can easily be removed, so that elaborate purification of the products is unnecessary.

The large number of synthesized compounds in combinatorial chemistry means that the efficiency of modern automated test systems can be fully exploited with regard to chemical diversity. Since, however, in contrast to classical active substance synthesis, the chemicals to be investigated are not available in any desired amount on synthesis by means of combinatorial chemistry, only a restricted number of test systems can be examined because of the amounts of chemicals required in the test systems.

Another disadvantage of present test systems, for example in research looking for active substances, in diagnostic methods, in environmental protection or crop protection, is that the reagents required for many test systems, such as enzymes, antibodies, receptors, fluorescent dyes, radioactively or otherwise labeled ligands, cytokines, activators, inhibitors or other reagents, are costly, difficult to prepare and/or not available in a quantity sufficient for the automated tests.

DE-A 44 35 727 describes an approach for reducing the reagents required for a test.

The disadvantage of this process is that the support for the measurements must first be produced in an elaborate multistage process.

Another disadvantage is that the reactions which can be carried out with this support material are confined to reactions linked to solid phases, such as reactant binding between antibodies, antigens, haptens or nucleic acids. It is not possible with this method to carry out reactions in solution.

It is an object of the present invention to develop a novel analytical measurement method which can be carried out without the stated disadvantages and provide it for research looking for active substances, diagnostic methods, environmental protection, crop protection, toxicology or combinatorial chemistry.

We have found that this object is achieved by using the solid support described at the outset for the measurement method.

It has been found that the surface tension which hinders further miniaturization of the present microtiter plate technique to ever smaller reaction cavities (=wells), because thereby forces such as adhesion of the reaction liquid to the surface of the microtiter plates or the capillary forces are of increasing importance, and thus make it impossible to fill the reaction cavities and thus carry out a measurement, in very small microtiter plate wells, can be utilized advantageously for the supports according to the invention.

Figure 3:
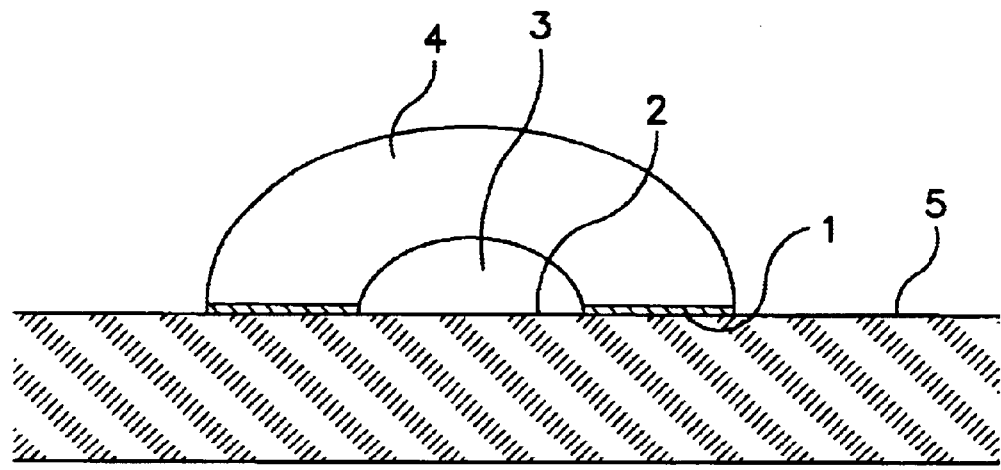
Figure 4:
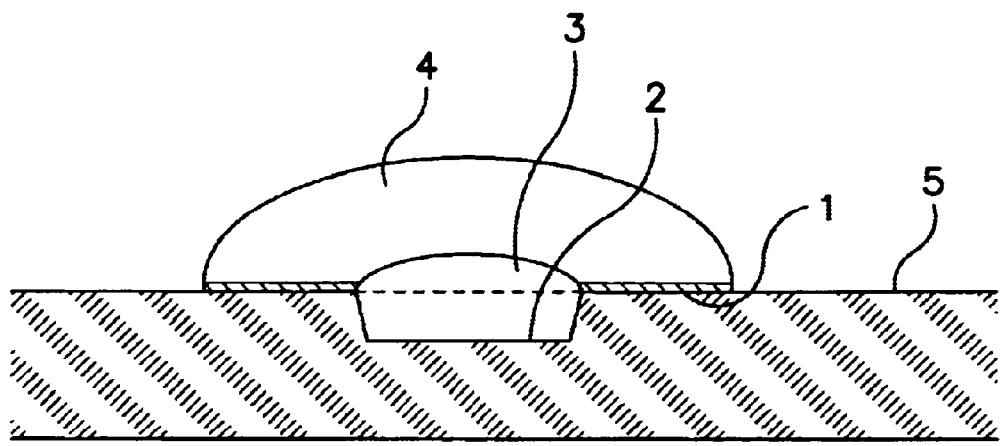

Hydrophilic measurement zones on the support mean areas on the support on which or in which the measurement is carried out after application of the reaction liquid and thus of the reactants (see number 2 in FIGS. 1, 3 and 4). They thus correspond to the wells in microtiter plates and are referred to hereinafter as "measurement zones or measurement points".

The hydrophilic measurement zones on the support are advantageously surrounded by a hydrophobic zone (see number 1 in FIGS. 1 to 4). This hydrophobic zone can be composed of at least one hydrophobic coating which covers the support completely or only partly with discontinuities. These discontinuities (see number 5 in FIGS. 1 to 4) are advantageously hydrophilic.

FIGS. 1 to 4 serve to illustrate the supports according to the invention by way of example.

The measurement zones, and the hydrophobic zones which separate them from one another (see number 1 in FIGS. 1 to 4), can be applied, for example, by microlithography, photoetching, microprinting or a micropunch technique or can be sprayed on using a mask technique. Photochemical processes which can be used to make the surfaces of plates or rolls specifically hydrophobic at particular points and hydrophilic at other points are known from the techniques for producing printing plates. It is possible with this technique to produce, for example, a grid of several thousand regularly arranged hydrophilic measurement zones (see number 2 in FIGS. 1, 3 and 4), surrounded by hydrophobic margins (see number 1 in FIGS. 1 to 4), in a simple manner on a support, eg. on a glass or metal plate. This may entail firstly one or more hydrophobic coatings being applied to the support, and subsequently the measurement zones being applied to the required points or, conversely, initially the hydrophilic measurement zones and then the hydrophobic zones, or both simultaneously, being applied. It is also possible to apply a plurality of hydrophilic measurement zones to the same point.

Figure 2:
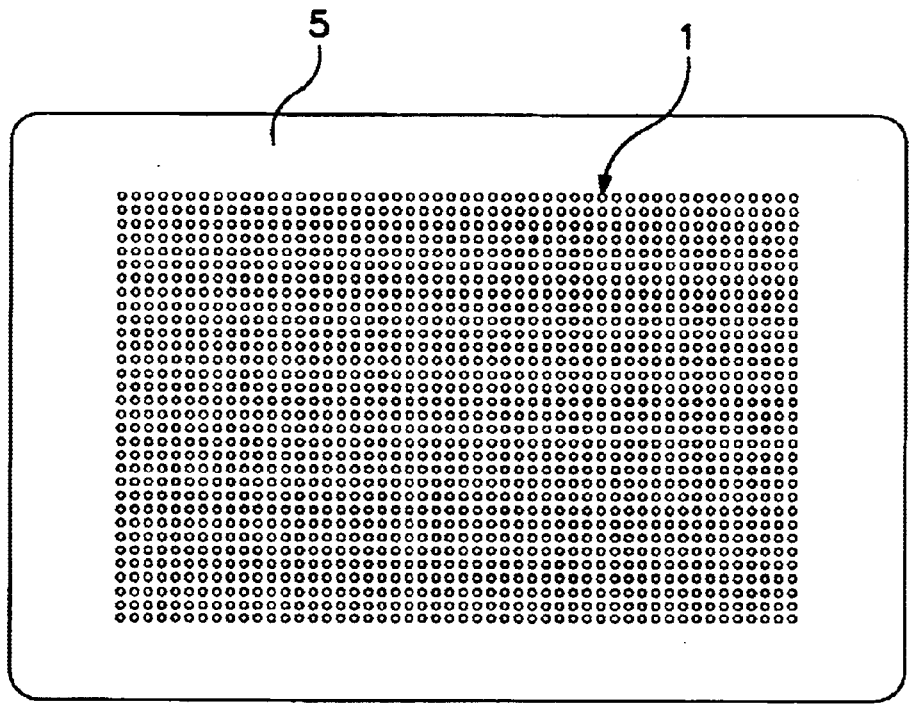

FIG. 2 depicts by way of example a support according to the invention having the size of a microtiter plate.

The measurement zones can have any desired shape, with circular measurement zones being preferred.

The hydrophobic coating or coatings may be applied coherently to the support or else be provided with discontinuities of any design. They may also be in the form of separate zones around the measurement zones, with hydrophobic rings separating the hydrophilic measurement zones from one another being preferred.

The hydrophobic coating or coatings are intended to prevent the measurement zones spreading into one another and thus to make accurate measurement of individual reaction mixtures possible.

It is possible in principle to apply any desired number of measurement points onto a support, but the number of measurement points per $cm^2$ is preferably greater than or equal to 10, particularly preferably greater than or equal to 15 and very particularly preferably greater than or equal to 20. Moreover, the reaction volumes applied are from a few nl up to some $\mu l$, with volumes of less than 5 $\mu l$ being preferred, and of less than or equal to 1 $\mu l$ being particularly preferred.

The measurement points can be applied in any desired grids to the support, and square or rectangular grids are preferred.

The inert solid support may consist of a level, planar plate of a block of the same type or of a sheet of any desired shape and size, which may have small depressions (see FIG. 4) at the measurement zone points, with flat supports (see FIG. 3) being preferred. Rectangular or square supports are preferred, and rectangular supports with the size of a standard microtiter plate (127.5 mm×85.5 mm) or integral multiples of microtiter plates, which can be larger or smaller, for example the Terasaki plates (81 mm×56 mm, 60 measurement points), are particularly preferred. The preferred size of the supports according to the invention has the advantage that all the peripherals of automated microtiter plate technology can be used without alteration.

The support may consist, for example, of materials such as glass, ceramic, quartz, metal, stone, wood, plastic, rubber, silicon, germanium or porcelain. The materials can be used in pure form, as mixtures, alloys or blends or in various layers or after coating with, for example, a plastic or a paint for producing the supports according to the invention. Transparent supports made of quartz, glass, plastic, germanium or silicon, which are suitable for all visual tests such as microscopic, camera-assisted and laser-assisted tests, are preferably produced.

Suitable transparent plastics are all amorphous plastic materials which [lacuna] in a single-phase or multiphase manner with identical refractive index as polymers of acrylonitrile/butadiene/styrene or in a multiphase manner with different refractive index, in which the domains of the plastic components form zones which are smaller than the wavelength of light, such as the block copolymers of polystyrene and butadiene (polystyrene/butadiene blends).

Particularly suitable transparent plastics which may be mentioned in this connection are polystyrene, styrene/acrylonitrile, polypropylene, polycarbonate, PVC (=polyvinyl chloride), poly(methyl methacrylate), polyesters, silicones, polyethylene/acrylate, polylactide or cellulose acetate, cellulose propionate, cellulose butyrate or mixtures thereof. Silicon or germanium supports are particularly suitable for applications in which detection or induction of the reaction using near infrared light is necessary.

The support according to the invention may also be designed in the form of a conveyor belt which, when the assays are automated, can move past the charging, incubation or detection stations.

One process for producing the supports according to the invention starts, for example, from ceramic, quartz or glass plates. The support is for this purpose expediently first cleaned with a cleaner, for example an alcohol, an alkaline cleaner or an acidic cleaner such as Reacalc® (which contains, according to the supplier Chemotec GmbH, phosphoric acid and surfactants). The cleaning can advantageously be improved by carrying it out in an ultrasonic bath. After cleaning, the support is dried, immediately or after rinsing with water and/or alcohol or with an alcohol/water mixture. The hydrophobic coating of the support takes place, for example, with a 1% strength hexadecyltrimethoxysilane solution in a solvent such as isopropanol/$H_2O$ (9:1) using a punch technique. The punch is briefly pressed on the glass slide to apply the 1% strength hexadecyltrimethoxysilane solution. The support is subsequently dried. The glass support is advantageously dried at elevated temperatures, ie. above 80° C. The support is preferably rinsed once again after drying to remove excess hexadecyltrimethoxysilane, for example with an alcohol/water mixture such as isopropanol/$H_2O$ (9:1).

This punch technique may be used to apply an additional surface loading in the region of the hydrophilic measurement points. This surface loading can be generated, for example, by applying proteins, acidic or basic polymers such as polylysine or acidic or basic molecules.

Methods suitable for applying sample material and reagents are all those able to meter amounts of liquid from a few nl to a few $\mu l$, such as techniques used in ink jet printers (see DE-A 40 24 544) or in flow cytometry, in cell sorters (Horan, P. K., Wheeless, L. L., Quantitative Single Analysis and Sorting, Science 198 (1977) 149–157). Drop formation can in this case take place by piezoelectric drop formation (ultrasound), piezoelectric drop ejection or ejection by evaporation (ink jet technique). It is possible to use systems with permanent drop production or systems which produce drops on demand.

These techniques can be used to place individual droplets in an accurately metered and targeted manner on the individual hydrophilic measurement points of the multianalysis surface of the support by, for example, moving the support under one or more nozzles, which are arranged in parallel, in accordance with the rhythm of the metered liquid and in accordance with the preset grid, It is also possible likewise to move the metering device, for example consisting of at least one nozzle, over the support in accordance with the rhythm of the metered liquid and in accordance with the preset grid.

It is possible with these techniques if necessary to place different reagents and/or individual cells on the predetermined sites (measurement points) on the support surface and bring about reaction thereof. It is advantageous that, with the small volumes preferred according to the invention, in the range from a few nanoliters to a few microliters, mixing of the reactants by diffusion takes place very quickly so that no special mechanical mixing device is necessary. It is also possible, before the addition of liquid droplets for carrying out the actual analysis, for certain ligands, eg. proteins or nucleic acids, to be present on the support in adsorbed or chemically bound form before metering in the measurement samples and the reagents.

Further advantages of the supports according to the invention are the saving of substances such as chemicals to be tested, enzymes, cells or other reactants, of time through a further increase in parallel reaction mixtures, which are automated where appropriate, of space and staff requirements, due to further miniaturization of the reaction mixtures and thus finally also of money.

The droplets placed on the supports may also be applied in the form of gel droplets which subsequently solidify where appropriate and thus reduce evaporation of the reaction liquid.

Evaporation of the reaction liquid (see number 3 in FIGS. 3 and 4) can also be reduced by coating with a hydrophobic liquid (see number 4 in FIGS. 3 and 4), in which case the hydrophobic coating or coatings act like an anchor (FIG. 3 and 4). Low-viscosity oils such as silicone oils are preferably used for the coating.

Evaporation can also be reduced by incubating the supports in an atmosphere which is virtually saturated with water vapor.

Reduction in evaporation is likewise possible by cooling the supports.

Evaporation can be reduced by using single elements of those mentioned or combinations thereof.

The supports according to the invention are suitable in principle for all analytical methods now carried out in microtiter plates, such as colorimetric, fluorimetric or densitometric methods. It is possible in these cases to use and measure light scattering, turbidity, wavelength-dependent light absorption, fluorescence, luminescence, raman scattering, ATR (=Attenuated Total Reflection), radioactivity, isotope labeling, pH shifts or ion shifts, advantageously alone or in combination, to mention only a few of the possible measured quantities here.

Analytical methods which can be carried out on the supports according to the invention and which may be mentioned here are the binding of antibodies to antigens, the interaction between receptors and ligands, the specific cleavage of substrate molecules by enzymes, the polymerase chain reaction (PCR), agglutination tests or the interaction between different or identical cell types such as enzyme assays, titration assays such as virus titration assays, erythrocyte or platelet aggregation assays, agglutination assays with latex beads, ELISA (=Enzyme-linked immunosorbent assay) or RIA (=Radioimmunoassay).

The supports according to the invention can be employed, for example, in diagnostic methods, in research looking for active substances, in combinatorial chemistry, in crop protection, in toxicology, in environmental protection, for example for cytotoxicological tests, in medicine or in biochemistry.

The supports according to the invention are particularly suitable for mass screening.

The supports according to the invention are particularly suitable for all modern image-acquiring and image-analyzing systems.

The following examples serve to illustrate the invention further without restricting it in any way.

EXAMPLE 1

Production of a support according to the invention from a glass slide

Firstly, the glass slide was cleaned with a 20% strength aqueous solution of an acidic cleaner (Reacalc® supplied by Chemotec GmbH) in an ultrasonic immersion bath for 10 minutes. The glass slide was subsequently rinsed with water and then with absolute ethanol and dried at about 23° C.

A micropunch was used to apply the hydrophobic coating in the form of hydrophobic rings (see FIGS. 1 to 4) on the hydrophilic support. The hydrophobic layer was applied using a 1% strength hexadecyltrimethoxysilane solution in isopropanol/$H_2O$ (9:1). The punch was dipped in the silane solution and then briefly, for about 5 sec, pressed on the support, and then the support was dried at 100° C. for 15 minutes. Excess silane solution was removed from the support by immersing the support in isopropanol/$H_2O$ (9:1) for about 1 minute. Two types of punches were used to apply 12 and 25, respectively, measurement points per square centimeter.

EXAMPLE 2

Protease inhibitor assay with the supports according to the invention

A protease inhibitor assay was carried out using a support produced by the process described in Example 1.

96 samples each comprising 100 nl of a solution of casein labeled with fluorescein isothiocyanate (20 μg/ml) in 10 mM tris/HCl buffer (pH 8.5) were applied, in a chamber with a relative humidity exceeding 95% using a micrometering system supplied by Microdrop, Norderstedt, to a slide produced as described above. The reaction droplets were arranged in 8 rows and 12 columns in a 2×2 mm grid in accordance with the hydrophobic zones (=barrier layers) applied by the punch. The width of the hydrophobic rings was 0.4 mm in each case.

Subsequently, 1 nl of each of various protease inhibitors in a concentration of 1 mM in 10 mM tris/HCl buffer (pH 8.5) was added to the reaction samples using the Microdrop apparatus. Addition took place precisely into the fluorescent-labeled casein solution which had previously been applied. One nanoliter of 10 mM tris/HCl buffer (pH 8.5) was used as control.

Finally, 10 nl of the protease trypsin in a concentration of 10 mg/ml in tris/HCl buffer (pH 8.5) were added to the reaction.

The reaction droplets were subsequently covered either with mineral oil, silicone oil or liquid paraffin, which was applied using the microdrop metering system, to reduce evaporation.

After incubation for 30 minutes, the assay was measured. This was done using an inverted fluorescence microscope for excitation, from the underside of the slide, with linearly polarized light in the range from 450 to 485 nm and for detection of fluorescence in the range from 515 to 530 nm. A coolable CCD camera in front of which there was a polarization filter which could be rotated by a motor was used for detection.

The anisotropy of polarization of the casein molecules was determined using the following equations:

$$A = \frac{I_{perpendicular} - I_{parallel}}{I_{perpendicular} + 2, \times I_{parallel}} \quad (I)$$

$$A = \frac{I_{perpendicular} - I_{parallel}}{I_{perpendicular} + I_{parallel}} \quad (II)$$

where:

| | |
|---|---|
| A | is the anisotropy |
| P | is the polarization |
| $I_{parallel}$ | is the measured intensity of the fluorescent light on polarization parallel to the polarization of the exciting light and |
| $I_{perpendicular}$ | is the measured intensity of the fluorescent light with crossed polarization filters. |

The anisotropy is a measure of the rotational diffusion coefficient of molecules and can be employed to estimate the hydrodynamic sizes of molecules (G. Weber, Biochemie, Vol. 51, 1952, 145–155).

On cleavage of the protein labeled with fluorescein isothiocyanate by the protease, a polarization in the range from 50 to $75 \times 10^{-3}$ was measured. On inhibition of the protease trypsin, the measured polarization was greater than $150 \times 10^{-3}$.

For parallel analysis of all 96 reaction mixtures, the complete measurement field with the 96 points was covered at one time with a lens of a stereo magnifier and was analyzed using an image-processing program.

EXAMPLE 3

Protease inhibitor assay with 1536 parallel measurement points

A trypsin inhibitor assay was carried out as described in Example 2 with 1536 parallel measurement points on the size of a microtiter plate (see FIG. 2).

We claim:

1. A solid support for analytical measurement methods which comprises an inert solid support material on which hydrophilic measurement zones are each surrounded by a hydrophobic zone and wherein a hydrophilic area separates the hydrophobic zones from one another, and where the number of measurement points applied per $cm^2$ of the support is greater than or equal to 10.

2. A sollid support as claimed in claim 1, wherein the hydrophilic measurement zones applied to the substrate are separated from one another by non-continuous hydrophobic zones in the forms of rings.

3. A support as claimed in claim 1, wherein the support material is glass, ceramic, quartz, metal, stone, plastic, rubber silicon or porcelain.

4. A support as claimed in claim 1, wherein a transparent support material selected from glass, quartz, silicon or plastic is used.

5. An analytical measurement method which comprises applying liquid analysis samples in the hydrophilic measurement zones of a support as claimed in claim 1, overlaying the hydrophilic measurement zones with a hydrophobic liquid and performing the analysis.

6. An analytical measurement method as claimed in claim 5, wherein the analytical measurement is carried out in an atmosphere which is virtually saturated with water vapor.

7. The analytical measurement method of claim 5, wherein the analytical measurement is carried out while cooling the support.

8. The analytical measurement method of claim 5 adapted for diagnostic methods, screening of active substances, combinatorial chemistry, crop protection, toxicology or environmental protection.

9. A sollid support as claimed in claim 1, wherein additional surface loading is applied to the hydrophilic measurement zones.

\* \* \* \* \*